United States Patent
Conway et al.

(10) Patent No.: US 11,157,528 B2
(45) Date of Patent: Oct. 26, 2021

(54) DEPENDENCY-DRIVEN WORKFLOW MANAGEMENT

(71) Applicant: International Business Machines Corporation, Armonk, NY (US)

(72) Inventors: Thomas Charles Conway, Heidelberg West (AU); Laura Rusu, Endeavour Hills (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 295 days.

(21) Appl. No.: 16/386,508

(22) Filed: Apr. 17, 2019

(65) Prior Publication Data

US 2020/0334276 A1    Oct. 22, 2020

(51) Int. Cl.
| | |
|---|---|
| *G06F 16/20* | (2019.01) |
| *G06F 16/28* | (2019.01) |
| *G06F 16/901* | (2019.01) |
| *G06F 9/38* | (2018.01) |
| *G06F 9/48* | (2006.01) |
| *G06F 16/24* | (2019.01) |

(52) U.S. Cl.
CPC .......... *G06F 16/288* (2019.01); *G06F 9/3838* (2013.01); *G06F 9/4881* (2013.01); *G06F 16/24* (2019.01); *G06F 16/9024* (2019.01)

(58) Field of Classification Search
None
See application file for complete search history.

(56) References Cited

U.S. PATENT DOCUMENTS

| | | | |
|---|---|---|---|
| 8,429,220 B2 | 4/2013 | Wilkinson et al. | |
| 8,520,002 B2 | 8/2013 | Stambaugh | |
| 8,799,282 B2 | 8/2014 | Goldenberg et al. | |
| 2009/0018882 A1 | 1/2009 | Burton et al. | |
| 2014/0100912 A1 | 4/2014 | Bursey | |
| 2015/0012921 A1* | 1/2015 | Lettow | G06F 9/4881 718/102 |

(Continued)

OTHER PUBLICATIONS

Ahmed, "A Survey on Bioinformatics Data and Service Integration Using Ontology and Declarative Workflow Query Language," Thesis, Wayne State University, Mar. 2007, 67 pages.

(Continued)

*Primary Examiner* — Jau Shya Meng
(74) *Attorney, Agent, or Firm* — Cantor Colburn LLP; Joseph Petrokaitis

(57) ABSTRACT

Aspects include querying, by a processing system, a workflow database for a desired target entity. The processing system traverses a dependency graph that defines one or more entity and action sequences of a workflow that result in creating the desired target entity based at least in part on failing to locate the desired target entity in the workflow database. The workflow can be a bioinformatics workflow to analyze one or more digital representations of biological data. The processing system queries the workflow database to determine an entity existence status of each entity in the one or more entity and action sequences. The processing system schedules execution of an associated action that outputs each entity identified as non-existent based at least in part on the entity existence status and the one or more entity and action sequences to create the desired target entity.

20 Claims, 6 Drawing Sheets

(56) References Cited

U.S. PATENT DOCUMENTS

2016/0004565 A1* 1/2016 Harper ................. G06F 9/4881
                                                                                         718/102
2016/0358103 A1* 12/2016 Bowers ................ G06F 9/4881

OTHER PUBLICATIONS

Cannataro et al. "Integrating ontology and workflow in PROTEUS, a grid-based problem solving environment for bioinformatics," Information Technology: Coding and Computing, 2004, Proceedings ITCC 2004, International Conference on. vol. 2. IEEE, 2004, 5 pages.

Conery et al., "Rule-based workflow management for bioinformatics," The VLDB Journal—The International Journal on Very Large Data Bases 14.3 (2005), pp. 318-329.

J. Leipzig, "A review of bioinformatic pipeline frameworks," Oxford—Briefings in Bioinformatics, 18(3), 2017, pp. 530-536.

Lemos et al., "Ontology-driven workflow management for biosequence processing systems," Database and Expert Systems Applications, Springer Berlin Heidelberg, 2004, 10 pages.

Muller et al., "Agentwork: a workflow system supporting rule-based workflow adaptation," Data & Knowledge Engineering 51.2 (2004), pp. 223-256.

S. Sadelin, et al., "Bpipe: a tool for running and managing bioinformatics pipelines," Oxford University Press, Bioinformatics Applications Note, vol. 28, No. 11 2012, pp. 1525-1526.

Yu et al., "A taxonomy of workflow management systems for grid computing," Journal of Grid Computing 3.3-4 (2005), pp. 171-200.

\* cited by examiner

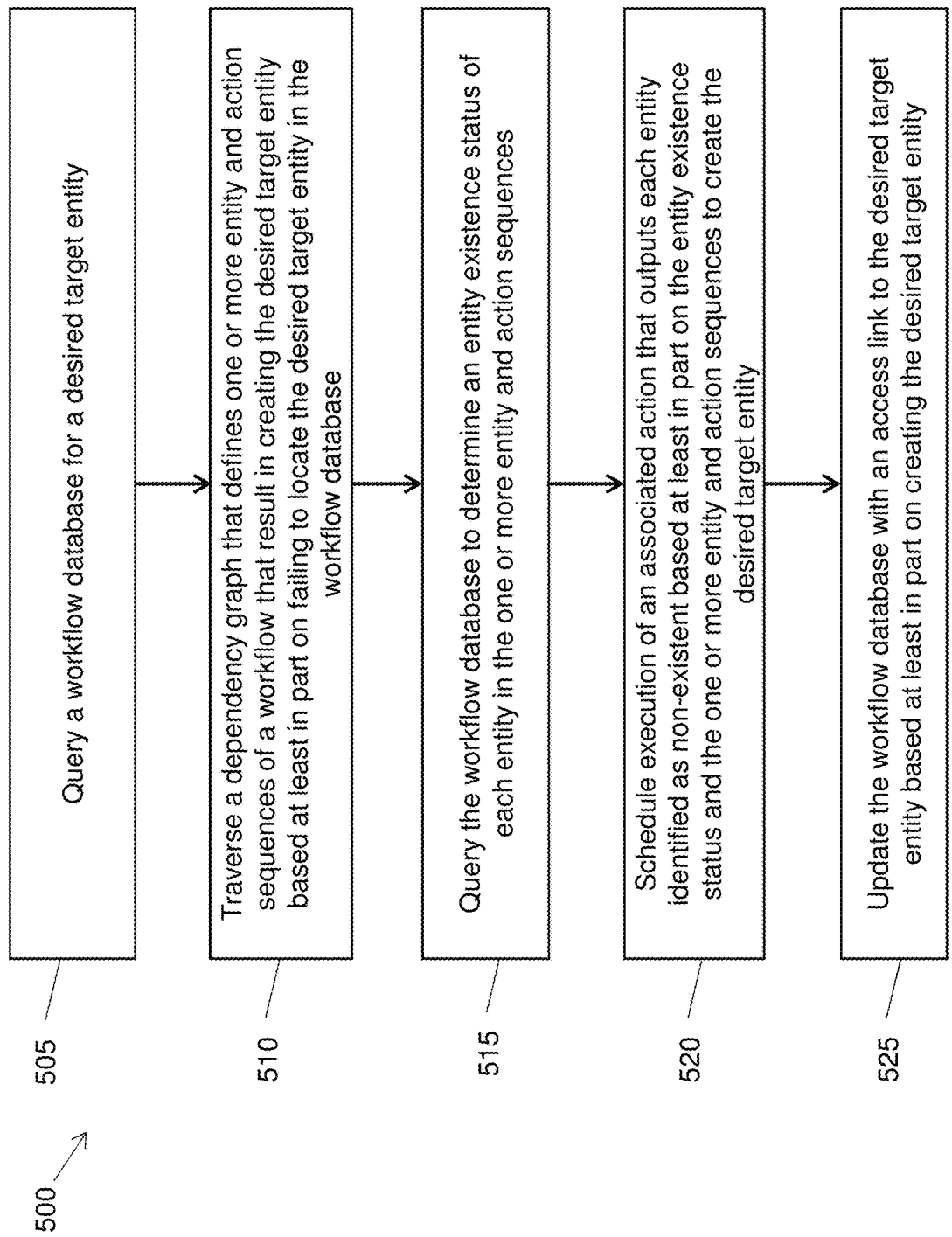

DEPENDENCY-DRIVEN WORKFLOW MANAGEMENT

BACKGROUND

The present invention relates to computer systems, and more particularly, to computer systems, computer-implemented methods, and computer program products configured to perform dependency-driven workflow management.

Data analysis processes performed by one or more computer systems can demand large quantities of processing resources and memory resources, which in turn consumes substantial electrical power. Complex analysis sequences can be defined as a workflow sequence, where dependencies exist between analysis actions. Some workflows can include configurable parameters and produce intermediate results. Changes to the parameters within the workflow or variations in external inputs may invalidate intermediate results, such that a full analysis sequence may need to be performed again upon a parameter or input update. In shared analysis systems, the processing and memory resource demands may be further increased where multiple users or systems attempt to execute workflow sequences that overlap in time.

SUMMARY

According to one or more embodiments of the present invention, a computer-implemented method includes querying, by a processing system, a workflow database for a desired target entity. The processing system traverses a dependency graph that defines one or more entity and action sequences of a workflow that result in creating the desired target entity based at least in part on failing to locate the desired target entity in the workflow database. The workflow can be a bioinformatics workflow to analyze one or more digital representations of biological data. The processing system queries the workflow database to determine an entity existence status of each entity in the one or more entity and action sequences. The processing system schedules execution of an associated action that outputs each entity identified as non-existent based at least in part on the entity existence status and the one or more entity and action sequences to create the desired target entity. An action scheduling status of the associated action is determined and scheduling of a redundant request to execute the associated action is prevented based at least in part on determining that the action is already scheduled for execution. The workflow database can be updated with an access link to the desired target entity based at least in part on creating the desired target entity.

Other embodiments of the invention implement the features of the above-described method in a computer system and in a computer program product.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 6 is a flow diagram illustrating a method according to a non-limiting embodiment of the invention.

Figure 1:
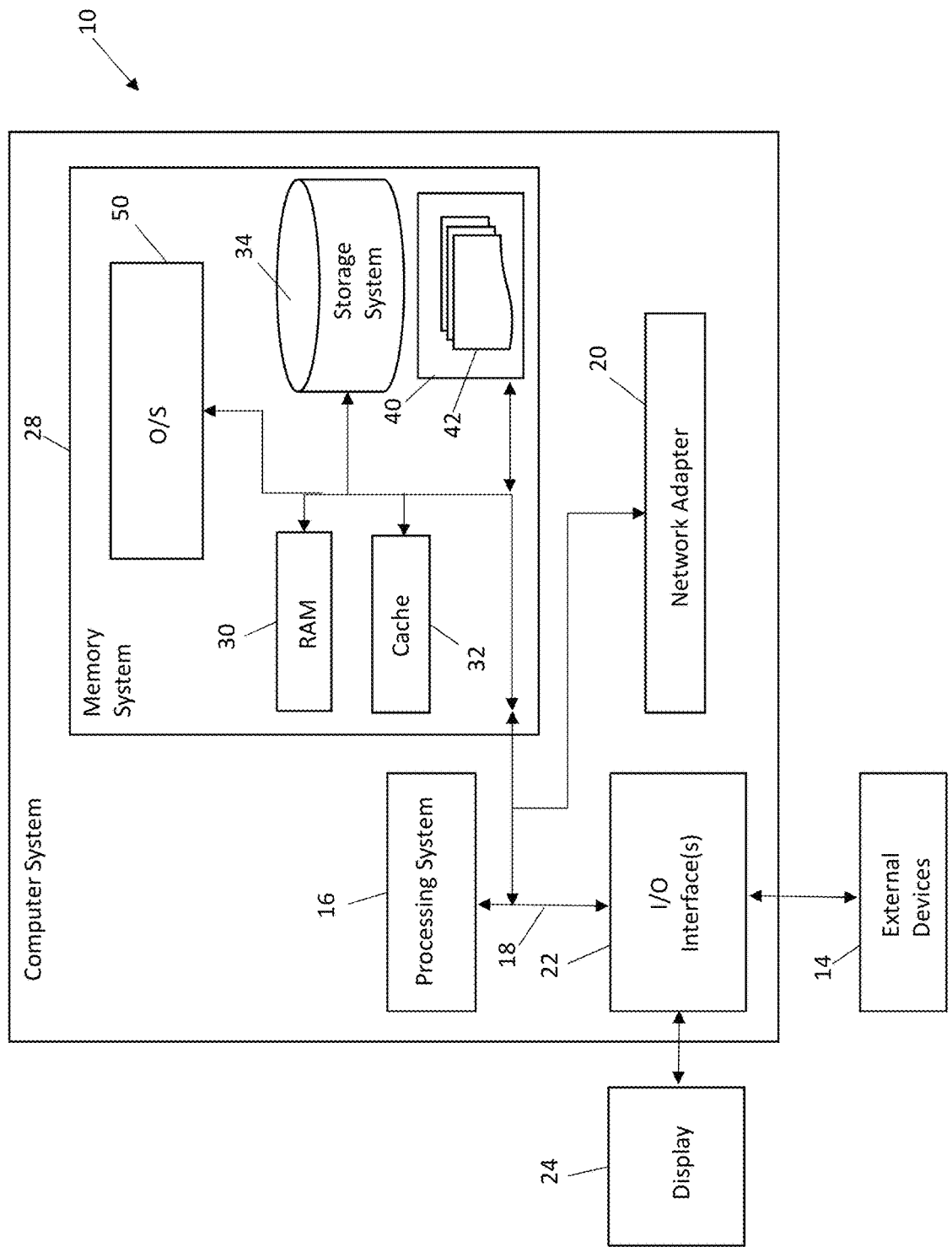
FIG. 1 is a block diagram illustrating a computer system in accordance with various embodiments of the invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can include any integer number greater than or equal to one, i.e. one, two, three, four, etc. The terms "a plurality" can include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, within data analysis processes, such as bioinformatics analysis, a workflow may be followed to perform a series of analysis steps from raw data through to a final analysis product. In short-read sequencing applications in the context of bioinformatics, this typically involves quality checks, mapping of sequencing data to a reference genome, identifying places where data indicates sequence variations compared to the reference, and other such actions. In the context of a public health/reference laboratory, the analysis may be performed on hundreds of samples per week, for instance. Downstream analysis can depend on intermediate results, and in many scenarios, the intermediate results may be relevant to multiple analyses. One approach to specifying workflows includes procedural definitions where analysis steps are defined in a sequence for turning source data into a final analysis product. In such a scenario, a user may regenerate some or all of the intermediate results. In the context of a public health laboratory dealing with hundreds of samples and performing analysis over a long baseline, redundant computations may be performed, which can consume large amounts of processing and memory resources.

Turning now to an overview of the aspects of the invention, one or more embodiments of the invention address the above-described shortcomings of the prior art by using a computer-implemented workflow management controller that specifies workflows using individual rules for generating results (e.g., intermediate and final outputs) rather than a linear step-by-step procedure. Using the rules and an associated database, results that already exist as entities can be tracked and results that are missing or incomplete due to dependencies can be identified to run a subset of analysis steps while avoiding redundant computation.

The above-described aspects of the invention address the shortcomings of the prior art by creating a dependency graph to identify dependencies between individual constituent analysis steps so that the execution can be automatically parallelized (e.g. on one or more processing systems). Using an associated database can also enable tracking of parameters or options used to generate results, so if a user runs analyses with different parameters, consistency of the results can be ensured. In the context of bioinformatics, a system can construct and evaluate bioinformatics workflows using an entity and an action. An entity is a piece of data (a record in a database, a file, etc.) that may be an input to an analysis or an output of an analysis. An action is a process, such as an analysis step, which turns one or more input entities into one or more result entities. Entities may have associated metadata, which can be referred to as properties. Actions may specify constraints on properties for inputs or outputs and may establish links between the inputs and outputs. A database can be maintained to track which entities exist and what properties are associated with the entities. Technical effects and benefits can include modular workflow management in a declarative manner which allows analysis actions to be performed without redundant computation and can increase opportunities parallel execution. Avoiding redundant computations can reduce demands for processing resources, memory resources, and electrical power consumption.

With reference now to FIG. 1, a computer system 10 is illustrated in accordance with a non-limiting embodiment of the present disclosure. More specifically, the computer system 10 can be programmed to implement the various aspects of the invention described in this detailed description. The computer system 10 may be based on the z/Architecture, for example, offered by International Business Machines Corporation (IBM). The architecture, however, is only one example of the computer system 10 and is not intended to suggest any limitation as to the scope of use or functionality of embodiments described herein. Regardless, computer system 10 is capable of being implemented and/or performing any of the functionality set forth hereinabove.

Computer system 10 is operational with numerous other computing system environments or configurations. Examples of well-known computing systems, environments, and/or configurations that may be suitable for use with computer system 10 include, but are not limited to, personal computer systems, server computer systems, thin clients, thick clients, cellular telephones, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Further, elements of the computer system 10 can be incorporated in one or more network devices to support computer network functionality, such as a network switch, a network router, or other such network support devices.

Computer system 10 may be described in the general context of computer system-executable instructions, such as program modules, being executed by the computer system 10. Generally, program modules may include routines, programs, objects, components, logic, data structures, and so on that perform particular tasks or implement particular abstract data types. Computer system 10 may be practiced in distributed cloud computing environments where tasks are performed by remote processing devices that are linked through a communications network. In a distributed computing environment, program modules may be located in both local and remote computer system storage media including memory storage devices.

As shown in FIG. 1, computer system 10 is shown in the form of a computing device, also referred to as a processing device. The components of computer system may include, but are not limited to, a processing system 16 including one or more processing cores or processing units, a memory system 28, and a bus 18 that operably couples various system components including memory system 28 to processing system 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 10 may include a variety of computer system readable media. Such media may be any available media that are accessible by computer system/server 10, and they include both volatile and non-volatile media, removable and non-removable media.

Memory system 28 can include an operating system (OS) 50, along with computer system readable media in the form of volatile memory, such as random access memory (RAM) 30 and/or cache memory 32. Computer system 10 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory system 28 may include at least one program product having a set (e.g., at least one) of program modules that are configured to carry out the functions of embodiments of the disclosure.

The OS 50 controls the execution of other computer programs and provides scheduling, input-output control, file and data management, memory management, and communication control and related services. The OS 50 can also include communication protocol support as one or more drivers to implement various protocol layers in a protocol stack (e.g., transmission control protocol/internet protocol (TCP/IP)) to support communication with other computer systems across one or more computer networks.

The storage system 34 can store a basic input output system (BIOS). The BIOS is a set of essential routines that initialize and test hardware at startup, start execution of the OS 50, and support the transfer of data among the hardware devices. When the computer system 10 is in operation, the processing system 16 is configured to execute instructions stored within the storage system 34, to communicate data to and from the memory system 28, and to generally control operations of the computer system 10 pursuant to the instructions.

Program/utility 40, having a set (at least one) of program modules 42, may be stored in memory system 28 by way of example, and not limitation, as well as the OS 50, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein at an application layer level in a communication protocol stack.

Computer system 10 may also communicate with one or more external devices 14 such as a keyboard, a pointing device, a display 24, etc.; one or more devices that enable a user to interact with computer system/server 10; and/or any devices (e.g., network card, modem, etc.) that enable computer system/server 10 to communicate with one or more other computing devices. Such communication can occur via Input/Output (I/O) interfaces 22. Still yet, computer system 10 can communicate with one or more networks such as a local area network (LAN), a general wide area network (WAN), and/or a public network (e.g., the Internet) via network adapter 20. As depicted, network adapter 20 communicates with the other components of computer system 10 via bus 18. It should be understood that although not shown, other hardware and/or software components could be used in conjunction with computer system 10. Examples include, but are not limited to: microcode, device drivers, redundant processing units, external disk drive arrays, RAID systems, tape drives, data archival storage systems, etc.

Figure 2:
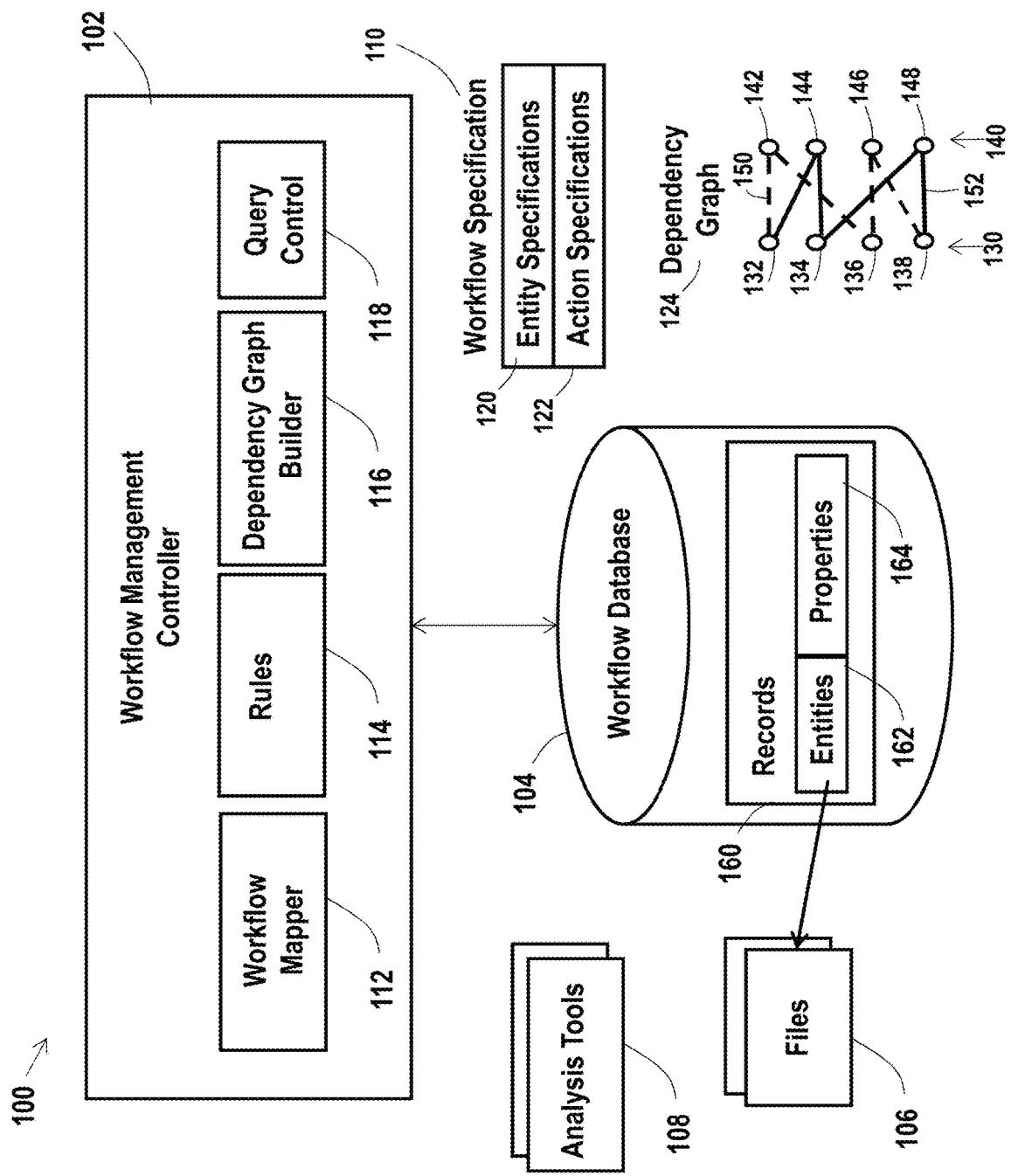
FIG. 2 is a block diagram of a system according to a non-limiting embodiment of the invention.

FIG. 2 depicts a block diagram of a system 100 that can be executed by the processing system 16 of FIG. 1 in accordance with aspects of the invention. The system 100 can include a workflow management controller 102 operable to interface with a workflow database 104, one or more files 106, a plurality of analysis tools 108, and one or more workflow specifications 110. The workflow management controller 102 can include a workflow mapper 112, rules 114, dependency graph builder 116, and a query control 118. The workflow mapper 112 can access the rules 114 to determine sequencing constraints between a plurality of entity specifications 120 and action specifications 122 of the workflow specifications 110. For example, the rules can define an order of actions and intermediate results needed to complete an analysis of source data to reach a targeted end result. The workflow mapper 112 can apply the rules 114 to the workflow specification 110 to determine which entities and actions must be accessed in a particular order. In some embodiments, the workflow mapper 112 can access a dependency graph 124 that defines dependencies between entities (as inputs and outputs) relative to actions, with further details defined in the entity specifications 120 and action specifications 122.

As an example, the dependency graph 124 can be organized as a bipartite graph with entity nodes 130 separated from action nodes 140 as two disjoint sets. For instance, entity nodes 130 can include entity node 132, 134, 136, and 138, while action nodes 140 include action node 142, 144, 146, and 148. There may be multiple entity and action sequences defined through the dependency graph 124. In the example of FIG. 2, an entity and action sequence 150 includes entity node 132 to action node 142 to entity node 136 to action node 146 to entity node 138. An entity and action sequence 152 includes entity node 132 to action node 144 to entity node 134 to action node 148 to entity node 138. Thus, if entity node 138 is a desired target entity, the entity and action sequence 150 or the entity and action sequence 152 may be performed to create an entity represented by entity node 138. The workflow database 104 can include a plurality of records 160 that track an existence status and may include links to a plurality of entities 162 with associated properties 164. The entities 162 can include one or more of the files 106 or data stored in the workflow database 104. The records 160 can be accessed through the query control 118 to determine whether a desired target entity with associated properties 164 has already been created.

Using the dependency graph 124, the workflow mapper 112 can identify members of the entity and action sequence 150, 152 and determine whether entities 162 associated with entity nodes 132-138 already exist or need to be created or updated. As an example, considering a scenario where entities associated with entity nodes 136 and 138 have not been created but entities 162 associated with entity nodes 132 and 134 have been created, then the workflow mapper 112 may select the entity and action sequence 152 to execute over the entity and action sequence 150, as fewer computational resources would likely be needed to create a desired target entity for entity node 138. Depending upon available computational resources, multiple sequences may be executed in parallel to further speed up the processing by analysis tools 108 performing actions associated with the action nodes 140.

Figure 3:
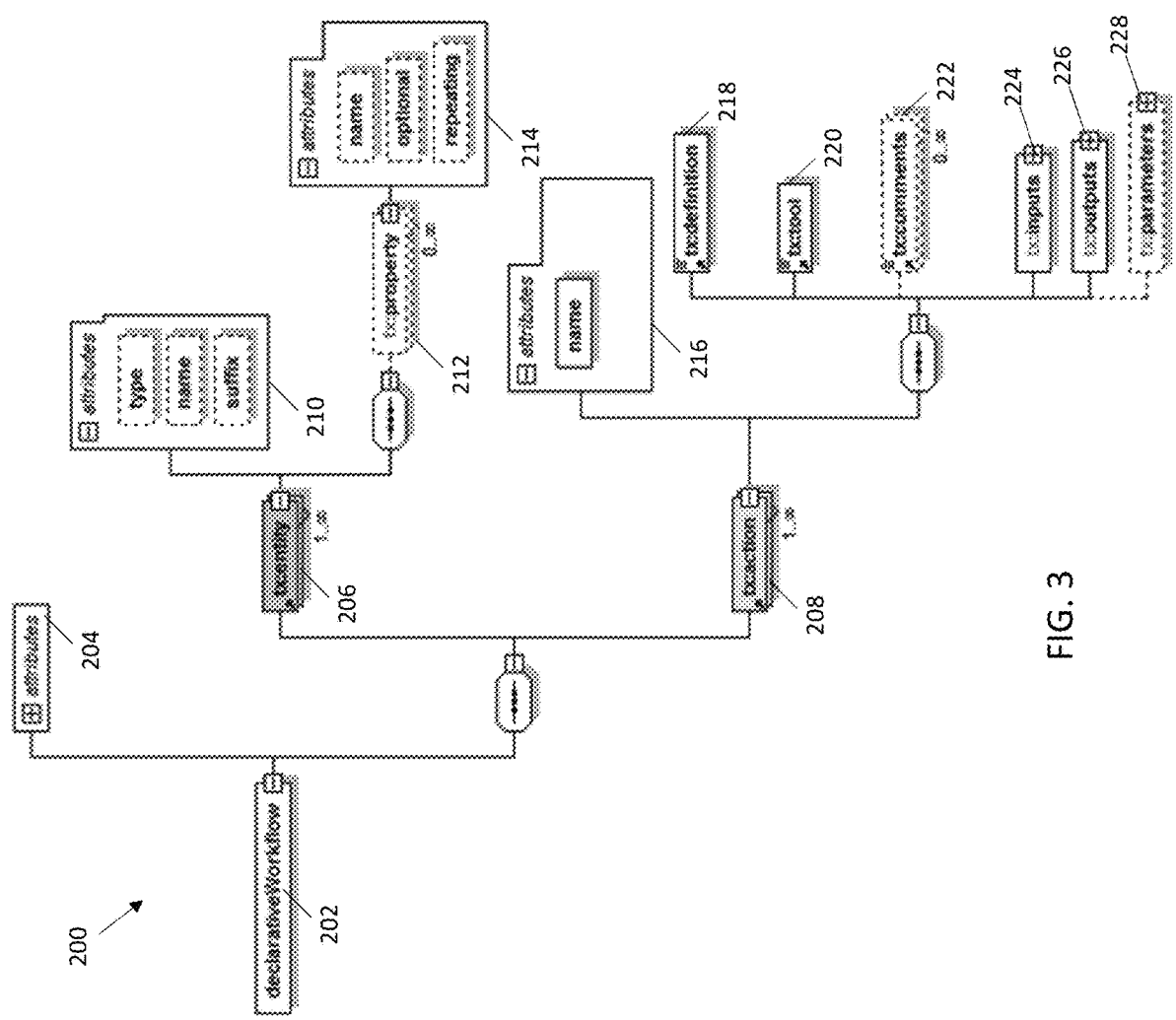
FIG. 3 is a block diagram of a structure of a workflow according to a non-limiting embodiment of the invention.
Figure 4:
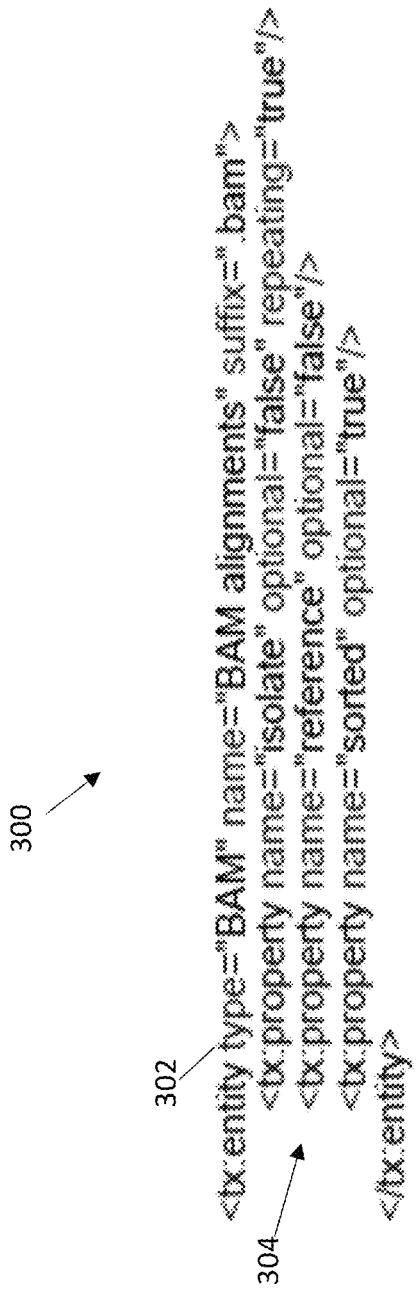
FIG. 4 is an example schema of an entity of a workflow according to a non-limiting embodiment of the invention.
Figure 5:
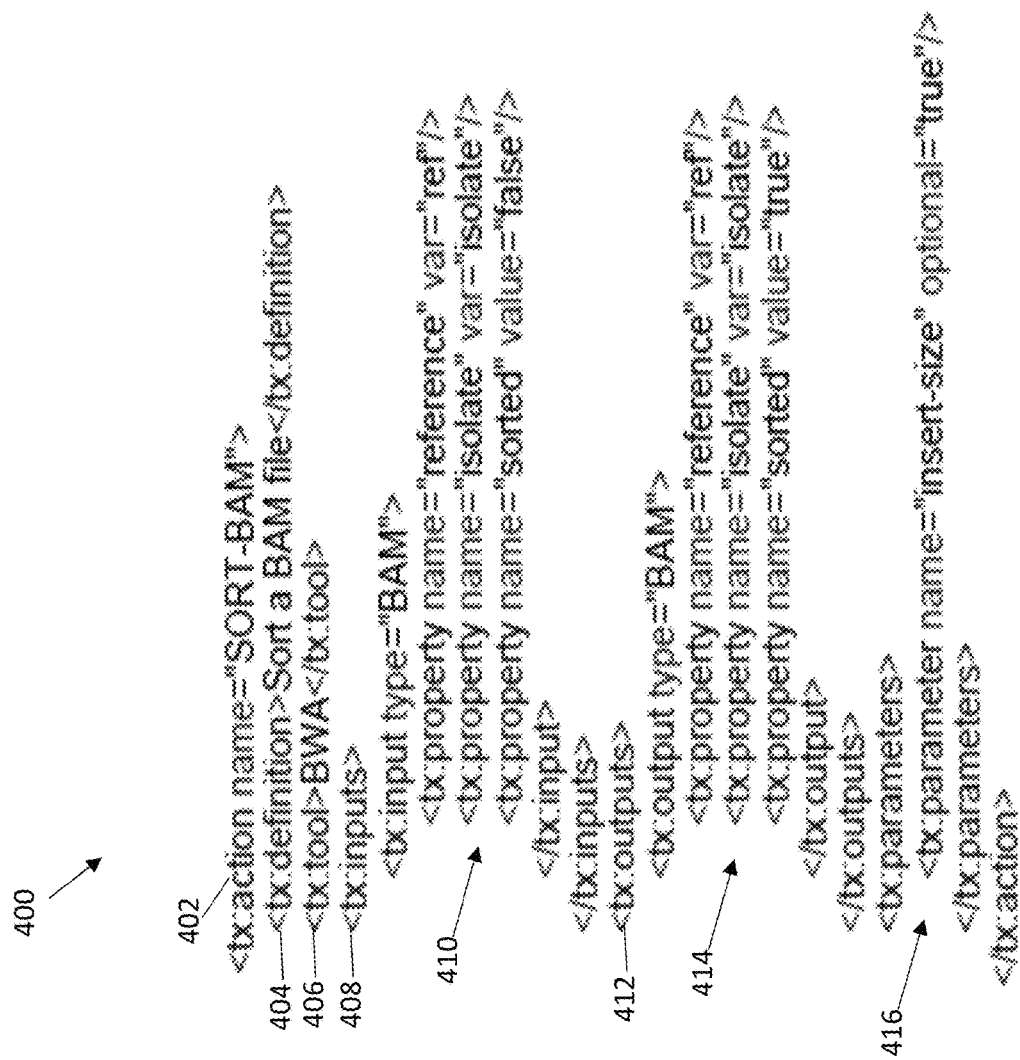
FIG. 5 is an example schema of an action of a workflow according to a non-limiting embodiment of the invention.

FIGS. 3-5 provide further detailed examples of a structure of a workflow 200, a schema 300 of an entity of the workflow 200, and a schema 400 of an action of the workflow 200. The workflow 200 can be specified in a machine-readable format, such as extensible markup language (XML). The examples of FIGS. 3-5 are described in relation to bioinformatics; however, other workflow and schema variations are contemplated. In the example of FIG. 3, the workflow 200 includes a workflow identifier 202 that has one or more workflow attributes 204, one or more entities 206, and one or more actions 208. Each of the one or more entities 206 can include one or more entity attributes 210 and properties 212. Each of the one or more entity attributes 210 can include, for example, an entity type, an entity name, and an entity suffix. Each of the properties 212 can include one or more property attributes 214, such as a property name, an optional status, and a repeating status. Each of the one or more actions 208 can include one or more attributes 216, such as an action name. The one or more actions 208 can also include various fields, such as a definition 218, a tool identifier 220, comments 222, action inputs 224, action outputs 226, and action parameters 228. The action inputs 224 and action outputs 226 can be used to define relationships with other entities, such as the entity nodes 130 of FIG. 2. Other fields can be added or removed from the structure of workflow 200.

As a further example with respect to bioinformatics, one of the files 106 of FIG. 2 may contain sequence reads from the sequencing of a bacterial isolate. Properties of the file can include the following property name, property value pairs: <species,&*Streptococcus pneumoniae*8>, <insert-size, 500>, <format, &paired-end8>, <isolate, &MDU-123-4568>, where the species property denotes the species of the isolate, insert-size and format, certain important properties of the way the sequencing was done, and the isolate property a uniquely identifying label for the isolate. As another example, one of the files 106 of FIG. 2 can contain a reference genome sequence for *Streptococcus pneumoniae*. It can have the property <reference, &*Streptococcus pneumoniae*8>. A typical action may be to align or map the reads to the reference yielding a binary alignment map (BAM) file. In such a case, the resulting BAM file, can inherit the species and isolate properties from reads, and the action can have a constraint that the species of the reads and the reference are the same. Further, the alignment action can make use of insert-size and format properties as parameters for alignment.

BAM files can provide a way of storing alignments between reads and sequences. Because BAM files may be merged, reads from more than one isolate may be stored in a BAM file. BAM files can be constrained to contain only reads aligned against the same reference. That is, if two BAM files are merged, then the BAM files can represent alignments against a single reference. Also, a BAM file may be sorted and/or indexed. Therefore, the description of BAM entities may look like the example of FIG. 4. FIG. 4 depicts a schema 300 of an entity of the workflow 200, such as a BAM file entity. The schema 300 can include entity attributes 302, such as an entity type of "BAM", an entity name of "BAM alignments", and an entity suffix of ".bam". The schema 300 can also include a plurality of properties 304, such as "isolate", "reference", and "sorted" with various states defined for determining whether the properties are optional or repeating. In embodiments, the entity specifications 120 of FIG. 2 can give a type of the file or database record, expected filename suffixes (where appropriate) and a list of properties, stating for each whether the property is mandatory and whether it may be repeating.

The action specifications 122 of FIG. 2 can identify types of input and output entities of an action, and relationships between properties. The specification can be declarative in nature. For some analysis steps, a BAM file may need to be sorted. An action to create a sorted version of an unsorted BAM file may specified as depicted in the example schema 400 of FIG. 5. The schema 400 includes an action name 402, a definition 404, a tool identifier 406, action inputs 408 defining input entity properties 410 (e.g., a reference property, an isolated property, and a sorted property), action outputs 412 defining output properties 414, and action parameters 416 (e.g., an insert-size property). In the example of FIG. 5, a "var" attribute can bind a value of a property to a name. Thus, given an input BAM file and an action to generate an output BAM file, the variable "ref" can be bound to the value of the reference property of the BAM input. When determining the set of properties for the output BAM file, the reference property can be bound to the previously set value of "ref". On the other hand, if the target is a sorted BAM file with a corresponding set of "isolate" and "reference", the variables can be set by the output specification and then the properties of the required input BAM (which may or may not exist) can be determined.

Embodiments can include using action specifications 122 to work out what input entities are required to produce a desired output entity, for instance, where the dependency graph builder 116 of FIG. 2 creates a dependency graph 124. As another example, the workflow management controller 102 of FIG. 2 can specify a desired target, for instance, a phylogenetic tree, with a desired set of properties (e.g., built with respect to a certain reference sequence and a given collection of isolates). If the target entity (with appropriate properties 164) exists in the workflow database 104, then no work needs to be done. If the target entity does not exist in entities 162, the action specifications 122 can be used to find an action that can produce the output entity. From this, a set of desired input entities can be constructed, each of which becomes a new target. This process can be repeated until a complete dependency graph 124 is constructed with existing entities 162 as sources and the original target as a sink. Once the dependency graph 124 has been constructed, a complete list of required actions can be composed. If simple sequential execution is desired, then a list may be composed in reverse by a breadth first traversal of the dependency graph 124 such that an action is not generated until all children have been generated. If a parallel execution environment is available (e.g. a cluster, or cloud), the dependency graph 124 may be analyzed to schedule independent work and add explicit dependencies (which can be supported by batch scheduling environments). When actions are scheduled (but not yet executed) the workflow database 104 of entities can be updated to reflect that although the entity is not yet present, it is pending. Thus, a concurrent use of the system 100 may not schedule redundant jobs. Embodiments also allow for recovery if the system 100 fails. Pending jobs can either be cleared, if manual recovery is desired by rescheduling of actions, or pending jobs can be automatically rescheduled. As actions are performed and result entities created, the workflow database 104 can be updated to track the entities 162.

Turning now to FIG. 6, a flow diagram of a process 500 is generally shown in accordance with an embodiment. The process 500 is described with reference to FIGS. 1-6 and may include additional steps beyond those depicted in FIG. 6. The process 500 can be performed by the processing system 16 of FIG. 1 executing the workflow management controller 102 of FIG. 2.

At block 505, the processing system 16 can query a workflow database 104 for a desired target entity. At block 510, the processing system 16 can traverse a dependency graph 124 that defines one or more entity and action sequences 150, 152 of a workflow 200 that result in creating the desired target entity based at least in part on failing to locate the desired target entity in the workflow database 104. The workflow 200 can include a plurality of entities 206 with corresponding properties 212 and a plurality of actions 208 that create or use the entities 206 and the corresponding properties 212. The workflow 200 can be a bioinformatics workflow to analyze one or more digital representations of biological data. The dependency graph 124 can be created based at least in part on an entity specification 120 of the workflow 200, an action specification 122 of the workflow 200, and a plurality of rules 114 that define an entity creation sequence. The actions 208 can include invoking one or more analysis tools 108 configured to produce one or more analysis outputs.

At block 515, the processing system 16 can query the workflow database 104 to determine an entity existence status of each entity in the one or more entity and action sequences. At block 520, the processing system 16 can schedule execution of an associated action that outputs each entity identified as non-existent based at least in part on the entity existence status and the one or more entity and action sequences 150, 152 to create the desired target entity. In some embodiments, the processing system 16 can determine an action scheduling status of the associated action and prevent scheduling of a redundant request to execute the associated action based at least in part on determining that the action is already scheduled for execution. Two or more actions of the one or more entity and action sequences 150, 152 can be scheduled to execute in parallel. At block 525, the processing system 16 can update the workflow database 104 with an access link to the desired target entity based at least in part on creating the desired target entity.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   querying, by a processing system, a workflow database for a desired target entity;
   traversing, by the processing system, a dependency graph that defines one or more entity and action sequences of a workflow that result in creating the desired target entity based at least in part on failing to locate the desired target entity in the workflow database, wherein the workflow comprises a bioinformatics workflow to analyze one or more digital representations of biological data;
   querying, by the processing system, the workflow database to determine an entity existence status of each entity in the one or more entity and action sequences;
   scheduling, by the processing system, execution of an associated action that outputs each entity identified as non-existent based at least in part on the entity existence status and the one or more entity and action sequences to create the desired target entity;
   determining an action scheduling status of the associated action;
   preventing scheduling of a redundant request to execute the associated action based at least in part on determining that the action is already scheduled for execution; and
   updating the workflow database with an access link to the desired target entity based at least in part on creating the desired target entity.

2. The computer-implemented method of claim 1, wherein the workflow comprises a plurality of entities with corresponding properties and a plurality of actions that create or use the entities and the corresponding properties.

3. The computer-implemented method of claim 2 further comprising creating the dependency graph based at least in part on an entity specification of the workflow, an action specification of the workflow, and a plurality of rules that define an entity creation sequence.

4. The computer-implemented method of claim 2, wherein the actions comprise invoking one or more analysis tools configured to produce one or more analysis outputs.

5. The computer-implemented method of claim 1 further comprising scheduling two or more actions of the one or more entity and action sequences to execute in parallel.

6. A system comprising:
   a workflow database;
   a processor; and
   a memory to store instructions, the instructions executed by the processor to perform a plurality of operations comprising:
      querying a workflow database for a desired target entity;
      traversing a dependency graph that defines one or more entity and action sequences of a workflow that result in creating the desired target entity based at least in part on failing to locate the desired target entity in the workflow database;
      querying the workflow database to determine an entity existence status of each entity in the one or more entity and action sequences; and
      scheduling execution of an associated action that outputs each entity identified as non-existent based at least in part on the entity existence status and the one or more entity and action sequences to create the desired target entity.

7. The system of claim 6, wherein the processing system is further configured to perform operations comprising updating the workflow database with an access link to the desired target entity based at least in part on creating the desired target entity.

8. The system of claim 6, wherein the processing system is further configured to perform operations comprising:
   determining an action scheduling status of the associated action; and
   preventing scheduling of a redundant request to execute the associated action based at least in part on determining that the action is already scheduled for execution.

9. The system of claim 6, wherein the workflow comprises a plurality of entities with corresponding properties and a plurality of actions that create or use the entities and the corresponding properties.

10. The system of claim 9, wherein the processing system is further configured to perform operations comprising creating the dependency graph based at least in part on an entity specification of the workflow, an action specification of the workflow, and a plurality of rules that define an entity creation sequence.

11. The system of claim 9, wherein the actions comprise invoking one or more analysis tools configured to produce one or more analysis outputs.

12. The system of claim 6, wherein the processing system is further configured to perform operations comprising scheduling two or more actions of the one or more entity and action sequences to execute in parallel.

13. The system of claim 6, wherein the workflow comprises a bioinformatics workflow to analyze one or more digital representations of biological data.

14. A computer program product comprising a computer readable storage medium having program instructions embodied therewith, the program instructions executable by a processing system to perform a plurality of operations comprising:
    querying a workflow database for a desired target entity;
    traversing a dependency graph that defines one or more entity and action sequences of a workflow that result in creating the desired target entity based at least in part on failing to locate the desired target entity in the workflow database, wherein the workflow comprises a bioinformatics workflow to analyze one or more digital representations of biological data;
    querying the workflow database to determine an entity existence status of each entity in the one or more entity and action sequences;
    scheduling execution of an associated action that outputs each entity identified as non-existent based at least in part on the entity existence status and the one or more entity and action sequences to create the desired target entity; and
    performing operations comprising updating the workflow database with an access link to the desired target entity based at least in part on creating the desired target entity.

15. The computer program product of claim 14, wherein the processing system is further configured to perform operations comprising:
    determining an action scheduling status of the associated action; and
    preventing scheduling of a redundant request to execute the associated action based at least in part on determining that the action is already scheduled for execution.

16. The computer program product of claim 14, wherein the workflow comprises a plurality of entities with corresponding properties and a plurality of actions that create or use the entities and the corresponding properties, and the workflow is a bioinformatics workflow to analyze one or more digital representations of biological data.

17. The computer program product of claim 14, wherein the workflow comprises a plurality of entities with corresponding properties and a plurality of actions that create or use the entities and the corresponding properties.

18. The computer program product of claim 17, wherein the processing system is further configured to perform operations comprising creating the dependency graph based at least in part on an entity specification of the workflow, an action specification of the workflow, and a plurality of rules that define an entity creation sequence.

19. The computer program product of claim 17, wherein the actions comprise invoking one or more analysis tools configured to produce one or more analysis outputs.

20. The computer program product of claim 14, wherein the processing system is further configured to perform operations comprising scheduling two or more actions of the one or more entity and action sequences to execute in parallel.

* * * * *